United States Patent
Frye et al.

(10) Patent No.: US 7,622,445 B2
(45) Date of Patent: Nov. 24, 2009

(54) MUTEINS OF FIBROBLAST GROWTH FACTOR 21

(75) Inventors: Christopher Carl Frye, Bargersville, IN (US); Lihua Huang, Carmel, IN (US); Radmila Micanovic, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 264 days.

(21) Appl. No.: 11/571,933

(22) PCT Filed: Aug. 25, 2005

(86) PCT No.: PCT/US2005/030215

§ 371 (c)(1),
(2), (4) Date: Jan. 11, 2007

(87) PCT Pub. No.: WO2006/028714

PCT Pub. Date: Mar. 16, 2006

(65) Prior Publication Data

US 2007/0299007 A1    Dec. 27, 2007

Related U.S. Application Data

(60) Provisional application No. 60/606,830, filed on Sep. 2, 2004.

(51) Int. Cl.
*C07K 14/50* (2006.01)
*A61K 38/18* (2006.01)

(52) U.S. Cl. .............................. 514/12; 514/2; 530/399

(58) Field of Classification Search ........................ None
See application file for complete search history.

(56) References Cited

U.S. PATENT DOCUMENTS

| 6,716,626 B1 | 4/2004 | Itoh et al. | |
| 7,491,697 B2 * | 2/2009 | Beals et al. | ................... 514/12 |

FOREIGN PATENT DOCUMENTS

| WO | WO 01/18172 | 3/2001 |
| WO | WO 01/18209 | 3/2001 |
| WO | WO 01/36640 | 5/2001 |
| WO | WO 01/38357 | 5/2001 |
| WO | WO 03/011213 | 2/2003 |
| WO | WO 03/059270 | 7/2003 |

OTHER PUBLICATIONS

Ciechanover, Aaron, et al., "N-terminal ubiquitnation: more protein substrates join in", Trends in Cell Biology (2004), 14(3): 103-106.

Nishimura, T., et al., "Identification of a Novel FGF, FGF-21, Preferentially Expressed in the Liver", Biochimica et Biophysica Acta (2000), 1492(1): 203-206.

Kharitonenkov, Alexei, et al., "FGF-21 As a Novel Metabolic Regulator", Journal of Clinical Investigation (2005), 115(6): 1627-1635.

* cited by examiner

*Primary Examiner*—Christine J Saoud
(74) *Attorney, Agent, or Firm*—Lynn D. Apelgren

(57) ABSTRACT

The present invention relates to novel muteins of human fibroblast growth factor-21 with reduced susceptibility for proteolytic degradation when expressed in yeast. Both protein and the respective encoding nucleic acid species are disclosed. The invention also embodies vectors and host cells for the propagation of said nucleic acid sequences and the production of said muteins. Also disclosed are methods for treating type 2 diabetes, obesity, or metabolic syndrome.

9 Claims, No Drawings

SEQUENCE LISTING

```
<160> NUMBER OF SEQ ID NOS: 2

<210> SEQ ID NO 1
<211> LENGTH: 181
<212> TYPE: PRT
<213> ORGANISM: homo sapiens

<400> SEQUENCE: 1

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 2
<211> LENGTH: 543
<212> TYPE: DNA
<213> ORGANISM: homo sapiens

<400> SEQUENCE: 2 cacccatcc ctgactccag tcctctcctg caattcgggg gccaagtccg gcagcggtac      60
ctctacacag atgatgccca gcagacagaa gcccacctgg agatcaggga ggatgggacg     120 gtgggggcg ctgctgacca gagccccgaa agtctcctgc agctgaaagc cttgaagccg      180
ggagttattc aaatcttggg agtcaagaca tccaggttcc tgtgccagcg gccagatggg     240
gccctgtatg gatcgctcca ctttgaccct gaggcctgca gcttccggga gctgcttctt     300
```

| | | | | |
|---|---|---|---|---|
| gaggacggat | acaatgttta | ccagtccgaa | gcccacggcc | tcccgctgca cctgccaggg | 360 |
| aacaagtccc | cacaccggga | ccctgcaccc | cgaggaccag | ctcgcttcct gccactacca | 420 |
| ggcctgcccc | ccgcactccc | ggagccaccc | ggaatcctgg | cccccagcc cccgatgtg | 480 |
| ggctcctcgg | accctctgag | catggtggga | ccttcccagg | gccgaagccc cagctacgct | 540 |
| tcc | | | | | 543 |

MUTEINS OF FIBROBLAST GROWTH FACTOR 21

CROSS-REFERENCE

This application claims the benefit of U.S. Provisional Application No. 60/606830 filed Sep. 2, 2004.

BACKGROUND OF THE INVENTION

1. Field of the Invention

The present invention relates to the identification of new muteins of fibroblast growth factor 21 that have reduced proteolytic degradation when expressed in yeast.

2. Description of the Related Art

Fibroblast growth factors are large polypeptides widely expressed in developing and adult tissues (Baird et al., *Cancer Cells*, 3:239-243, 1991) and play crucial roles in multiple physiological functions including angiogenesis, mitogenesis, pattern formation, cellular differentiation, metabolic regulation and repair of tissue injury (McKeehan et al., *Prog. Nucleic Acid Res. Mol. Biol.* 59:135-176, 1998). According to the published literature, the FGF family now consists of at least twenty-three members, FGF-1 to FGF-23 (Reuss et al., *Cell Tissue Res.* 313:139-157 (2003).

Fibroblast growth factor-21 (FGF-21) has been reported to be preferentially expressed in the liver (Nishimura et al., *Biochimica et Biophysica Acta*, 1492:203-206, (2000); WO01/36640; and WO01/18172) and described as a treatment for ischemic vascular disease, wound healing, and diseases associated with loss of pulmonary, bronchia or alveolar cell function and numerous other disorders. More recently, FGF-21 has been shown to stimulate glucose-uptake in mouse 3T3-L1 adipocytes in the presence and absence of insulin, and to decrease fed and fasting blood glucose, triglycerides, and glucagon levels in ob/ob and db/db mice and 8 week old ZDF rats in a dose-dependant manner, thus, providing the basis for the use of FGF-21 as a therapy for treating diabetes and obesity (WO03/011213).

The development of recombinant DNA technology has made possible the production of foreign products such as muteins of FGF-21 in host cells in which exogenous DNA sequences coding for those products have been introduced. The advantage of this technology is that products can be produced in high yields, in highly purified form, with low risk of contamination such as viral contamination. These recombinant techniques have been widely used for the production of recombinant proteins in prokaryotic as well as eukaryotic host cells.

However, the large-scale production of recombinant products by these techniques is still limited, due to problems of expression efficiency of these exogenous DNA sequences and also to vector instability. Recombinant products produced in heterologous eukaryotic hosts usually differ from their naturally-occurring counterpart in their glycosylation content. Moreover, recombinant products are also susceptible to intracellular proteolytic degradation by the host cell in which they are made. It is known that certain amino acid sequences are prone to degradation by proteolytic enzymes which usually has an adverse effect on protein activity. This susceptibility is due in part to the secondary and tertiary structure of the protein, exposing certain amino acids present on the surface of proteins to attack by proteolytic enzymes (Leszczynski et al., *Science* 234:849, 1986).

The present invention solves the problem of proteolytic degradation of FGF-21 by providing muteins of FGF-21 with reduced susceptibility for proteolytic degradation, wherein one or more protease labile amino acids are substituted by protease non-labile amino acid(s). Applicants have found that the FGF-21 muteins with reduced susceptibility for proteolytic degradation can be produced in industrial yeast fermentation conditions and maintain the biological activity necessary to be useful to treat subjects with disorders including, but not limited to, type 2 diabetes, obesity, and metabolic syndrome.

BRIEF SUMMARY OF THE INVENTION

In a first embodiment, the present invention provides muteins of human FGF-21, or a biologically active peptide thereof, comprising the substitution of Leu 153 with an amino acid selected from the group consisting of consisting of Gly, Ala, Val, Pro, Phe, Tyr, Trp, Ser, Thr, Asn, Asp, Gln, Glu, Cys, Met, or Ile, wherein the numbering of the amino acids is based on SEQ ID NO:1 and wherein said mutein has reduced susceptibility for proteolytic degradation when expressed in yeast compared to wild-type human FGF-21.

A second embodiment of the present invention provides muteins of human FGF-21, or a biologically active peptide thereof, comprising the substitution of Ala 154 with an amino acid selected from the group consisting of Gly, Val, Pro, Phe, Tyr, Trp, Ser. Thr, Asn, Asp, Gln, Glu, Cys, Met, Leu, or Ile, wherein the numbering of the amino acids is based on SEQ ID NO:1 and wherein said mutein has reduced susceptibility for proteolytic degradation when expressed in yeast compared to wild-type human FGF-21.

A third embodiment of the present invention provides muteins of human FGF-21 or a biologically active peptide thereof, comprising the substitution of Arg 96 with an amino acid selected from the group consisting of Gly, Ala, Val, Pro, Phe, Tyr, Trp, Ser, Thr, Asn, Asp, Gln, Glu, Cys, Met, or Ile, wherein the numbering of the amino acids is based on SEQ ID NO:1 and wherein said mutein has reduced susceptibility for proteolytic degradation when expressed in yeast compared to wild-type human FGF-21.

A fourth embodiment of the present invention provides muteins of human FGF-21, or a biologically active peptide thereof, comprising the substitution of Gly 174, Arg 175, and Pro 177 with Ala, wherein the numbering of the amino acids is based on SEQ ID NO:1 and wherein said mutein has reduced susceptibility for proteolytic degradation when expressed in yeast compared to wild-type human FGF-21.

A fifth embodiment of the present invention provides a mutein of human FGF-21, or a biologically active peptide thereof, comprising the substitution of Ser181 with Gly, wherein the numbering of the amino acids is based on SEQ ID NO:1 and wherein said mutein has reduced susceptibility for proteolytic degradation when expressed in yeast compared to wild-type human FGF-21.

Another embodiment of the present invention is a combination of the first, second, third, fourth, or fifth embodiments in a mutein of FGF-21. It is recognized that any permutation of these embodiments is contemplated by the present invention.

Yet another embodiment of the present invention is a combination of the first, second, third or fourth embodiments with other muteins of FGF-21 such as muteins with reduced O-glycosylation and muteins with improved pharmaceutical stability. It is recognized that any combination of these embodiments is contemplated by the present invention.

Other embodiments are drawn to polynucleotides encoding the muteins of the first, second, third and fourth embodiments, a vector containing said polynucleotides and a host cell carrying said vector. Another embodiment is drawn to processes to produce a polypeptide, to produce cells capable of producing said polypeptide and to produce a vector containing DNA encoding said polypeptide.

Yet another embodiment is drawn to methods of treating a patient exhibiting one or more of obesity, type II diabetes, insulin resistance, hyperinsulinemia, glucose intolerance, hyperglycemia, or metabolic syndrome comprising administering to said patient in need of such treatment a therapeutically effective amount of a human FGF-21 mutein of the first, second, third or fourth embodiment.

DETAILED DESCRIPTION OF THE INVENTION

For purposes of the present invention, as disclosed and claimed herein, the following terms are as defined below.

FGF-21 is a 208 amino acid polypeptide containing a 27 amino acid leader sequence. Human FGF-21 has ~79% amino acid identity to mouse FGF-21 and ~80% amino acid identity to rat FGF-21. Human FGF-21 is the preferred polypeptide template for the muteins of the present invention but it is recognized that one with skill in the art could readily make muteins based on an alternative mammalian FGF-21 polypeptide sequence.

The amino acid positions of the muteins of the present invention are determined from the mature human 181 amino acid FGF-21 polypeptide as shown below (SEQ ID NO:1):

```
1                                       10                                      20
His Pro Ile Pro Asp Ser Ser Pro Leu Leu Gln Phe Gly Gly Gln Val Arg Gln Arg Tyr 30                                      40
Leu Tyr Thr Asp Asp Ala Gln Gln Thr Glu Ala His Leu Glu Ile Arg Glu Asp Gly Thr 50                                      60
Val Gly Gly Ala Ala Asp Gln Ser Pro Glu Ser Leu Leu Gln Leu Lys Ala Leu Lys Pro 70                                      80
Gly Val Ile Gln Ile Leu Gly Val Lys Thr Ser Arg Phe Leu Cys Gln Arg Pro Asp Gly 90                                      100
Ala Leu Tyr Gly Ser Leu His Phe Asp Pro Glu Ala Cys Ser Phe Arg Glu Leu Leu Leu 110                                     120
Glu Asp Gly Tyr Asn Val Tyr Gln Ser Glu Ala His Gly Leu Pro Leu His Leu Pro Gly 130                                     140
Asn Lys Ser Pro His Arg Asp Pro Ala Pro Arg Gly Pro Ala Arg Phe Leu Pro Leu Pro 150                                     160
Gly Leu Pro Pro Ala Leu Pro Glu Pro Pro Gly Ile Leu Ala Pro Gln Pro Pro Asp Val 170                                     180
Gly Ser Ser Asp Pro Leu Ser Met Val Gly Pro Ser Gln Gly Arg Ser Pro Ser Tyr Ala

Ser
```

The corresponding DNA sequence coding for the mature human 181 amino acid FGF-21 polypeptide is (SEQ ID NO:2):

```
CACCCCATCCCTGACTCCAGTCCTCTCCTGCAATTCGGGGGCCAAGTCCG

GCAGCGGTACCTCTACACAGATGATGCCCAGCAGACAGAAGCCCACCTGG

AGATCAGGGAGGATGGGACGGTGGGGGGCGCTGCTGACCAGAGCCCCGAA

AGTCTCCTGCAGCTGAAAGCCTTGAAGCCGGGAGTTATTCAAATCTTGGG

AGTCAAGACATCCAGGTTCCTGTGCCAGCGGCCAGATGGGGCCCTGTATG
```

```
                                            -continued
GATCGCTCCACTTTGACCCTGAGGCCTGCAGCTTCCGGGAGCTGCTTCTT

GAGGACGGATACAATGTTTACCAGTCCGAAGCCCACGGCCTCCCGCTGCA

CCTGCCAGGGAACAAGTCCCCACACCGGGACCCTGCACCCCGAGGACCAG

CTCGCTTCCTGCCACTACCAGGCCTGCCCCCCGCACTCCCGGAGCCACCC

GGAATCCTGGCCCCCCAGCCCCCCGATGTGGGCTCCTCGGACCCTCTGAG

CATGGTGGGACCTTCCCAGGGCCGAAGCCCCAGCTACGCTTCC
```

Amino acids are identified using the three-letter code or alternatively are designated using the standard one letter code. Mutations are designated by the three-letter code for the original amino acid, followed by the amino acid number, followed by the three-letter code for the replacement amino acid. The numerical designations of each mutein is based on the 181 amino acid sequence of mature, wild-type, human FGF-21. For example, a substitution for leucine at position 153 (i.e. Leu153) with the non-polar/hydrophobic amino acid, isoleucine (Ile), is designated as Leu153Ile or L153I. In a similar fashion, the double substitution for leucine at position 118 and alanine at position 134 (Leu118, Ala134) with the sulfur containing amino acid, cysteine (Cys) is designated as Leu118Cys/Ala134Cys or L118C/A134C.

A human FGF-21 mutein is defined as comprising human FGF-21 in which at least one amino acid of the wild-type mature protein has been substituted by another amino acid. Examples of FGF-21 muteins are described in U.S. patent applications 60/528,582, and P-16824 (Lilly docket #) herein incorporated by reference. Generally speaking, a mutein possesses some modified property, structural or functional, of the wild-type protein. For example, the mutein may have enhanced or improved physical stability in concentrated solutions (e.g., less hydrophobic mediated aggregation), while maintaining a favorable bioactivity profile. The mutein may possess increased compatibility with pharmaceutical preservatives (e.g., m-cresol, phenol, benzyl alcohol), thus enabling the preparation of a preserved pharmaceutical formulation that maintains the physiochemical properties and biological activity of the protein during storage. The mutein may have reduced O-glycosylation when expressed in yeast. The mutein may have a reduced susceptibility for proteolytic degradation. For example, many proteins expressed in yeast are susceptible to proteolytic degradation by proteolytic enzymes present in the yeast host cell. As used herein, these terms are not limiting, it being entirely possible that a given mutein has one or more modified properties of the wild-type protein.

A "therapeutically-effective amount" is the minimal amount of an active agent necessary to impart therapeutic benefit to a patient. For example, a "therapeutically-effective amount" to a patient suffering or prone to suffer or to prevent it from suffering from type II diabetes, obesity, or metabolic syndrome is such an amount which induces, ameliorates or otherwise causes an improvement in the pathological symptoms, disease progression, physiological conditions associated with or resistance to succumbing to the afore mentioned disorders. For the purposes of the present invention a "subject" or "patient" is preferably a human.

Type II diabetes is characterized by excess glucose production in spite of the availability of insulin, and circulating glucose levels remain excessively high as a result of inadequate glucose clearance.

Glucose intolerance can be defined as an exceptional sensitivity to glucose.

Hyperglycemia is defined as an excess of sugar (glucose) in the blood.

Hypoglycemia, also called low blood sugar, occurs when your blood glucose level drops too low to provide enough energy for your body's activities.

Hyperinsulinemia is defined as a higher-than-normal level of insulin in the blood.

Insulin resistance is defined as a state in which a normal amount of insulin produces a subnormal biologic response.

Obesity, in terms of the human subject, can be defined as that body weight over 20 percent above the ideal body weight for a given population (R. H. Williams, Textbook of Endocrinology, 1974, p. 904-916).

Metabolic syndrome can be defined as a cluster of at least three of the following signs: abdominal fat—in most men, a 40-inch waist or greater; high blood sugar—at least 110 milligrams per deciliter (mg/dl) after fasting; high triglycerides—at least 150 mg/dL in the bloodstream; low HDL—less than 40 mg/dl; and, blood pressure of 130/85 or higher.

The present invention provides muteins with reduced susceptibility for proteolytic degradation when expressed in yeast compared to native FGF-21. Applicants have discovered that if one purifies human FGF-21 from a relatively large scale yeast fermentation culture, numerous degradation products are observed and separated on preparative RP-HPLC. The primary degradation fragments are residues 5-181, 5-153, and 5-96 wherein the numbering of the amino acids is based on SEQ ID NO:1. Other minor degradation fragments identified by Mono Q chromatography are residues 5-174, 5-175, and 5-177. Fragment 5-181 was disclosed in U.S. patent application 60/528,582 where it was shown that elimination of the first four amino acids from the N-terminus of FGF-21 does not adversely affect its biological activity, as measured in the 3T3L adipocyte glucose uptake assay. Thus, fragment 5-181 is not within the scope of the present invention. However, the other identified degradation fragments of human FGF-21 have impaired biological activity or are completely devoid of biological activity and muteins of FGF-21 that quantitatively reduce the above fragments by reducing the susceptibility to proteolytic degradation are within the scope of the present invention.

Therefore, in a first preferred embodiment, the present invention provides muteins of human FGF-21, or a biologically active peptide thereof, comprising the substitution of Leu 153 with an amino acid selected from the group consisting of Gln, Glu, Met, or Ile, wherein the numbering of the amino acids is based on SEQ ID NO:1 and wherein said mutein has reduced susceptibility for proteolytic degradation when expressed in yeast compared to wild-type human FGF-21. Preferred muteins of the first embodiment are Leu153Gln, Leu153Glu, and Leu153Met. The most preferred mutein of the first embodiment is Leu153Ile.

Mutating Ala 154 may also provide protection for Leu 153 from proteolytic degradation by steric interference or conformation change of the protein. Thus, a second embodiment of the present invention provides muteins of human FGF-21, or a biologically active peptide thereof, comprising the substitution of Ala 154 with an amino acid selected from the group consisting of Gly, Val, Ser, or Thr, wherein the numbering of the amino acids is based on SEQ ID NO:1 and wherein said mutein has reduced susceptibility for proteolytic degradation when expressed in yeast compared to wild-type human FGF-21. Preferred muteins of the second embodiment are Ala154Gly, Ala154Val, Ala154Ser, and Ala154Thr.

The proteolytic cleavage at Arg 96 is likely due to a trypsin-like enzyme since trypsin cleaves amide and ester bonds of Arg. It follows then that an isosteric change at Arg 96 with either Gln or Glu results in a mutein with reduced susceptibility for proteolytic degradation. A third embodiment of the present invention provides muteins of human FGF-21, or a biologically active peptide thereof, comprising the substitution of Arg 96 with an amino acid selected from the group consisting of Gln or Glu, wherein the numbering of the amino acids is based on SEQ ID NO:1 and wherein said mutein has reduced susceptibility for proteolytic degradation when expressed in yeast compared to wild-type human FGF-21. Preferred muteins of the third embodiment are Arg96Gln and Arg96Glu.

Although the proteolytic degradation products resulting from the cleavage at residues 174, 175, or 177 are relatively minor degradation fragments, it is still beneficial to the manufacturing process to provide a product of high integrity, containing as few impurities as possible. Accordingly, a fourth embodiment of the present invention are muteins of human FGF-21, or a biologically active peptide thereof, comprising the substitution of Gly 174, Arg 175, and Pro 177 with the aliphatic amino acid Ala, wherein the numbering of the amino acids is based on SEQ ID NO:1 and wherein said mutein has reduced susceptibility for proteolytic degradation when expressed in yeast compared to wild-type human FGF-21. Preferred muteins of the third embodiment are Gly174Ala, Arg175Ala, and Pro177Ala.

Alternatively, the cleavage at residues 174, 175, or 177 may be the result of yeast Carboxypeptidase Y activity that cleaves all C-terminal residues, however, very slowly if Rn=Gly. Thus, the preferred mutein to prevent this type of degradation is S181G. Additionally, applicants have discovered that the removal of more than 4 amino acids from the C-terminus of FGF-21 results in a fragment that is biologically inactive.

Another embodiment of the present invention is the combination of the first, second, third, or fourth embodiment with each other in any combination contemplated. For example, Leu153Ile is combined with Arg96Gln or Arg96Glu or Ala154Gly is combined with Arg96Gln. These examples are not limiting and any combination of the first, second, third, or fourth embodiments are within the scope of the present invention.

Furthermore, an embodiment of the present invention is the combination of the first, second, third, or fourth embodiments with additional muteins of human FGF-21 previously disclosed. For example, P16824 disclosed muteins of human FGF-21 comprising the substitution of any amino acid except Ser or Thr for Ser 167, wherein the numbering of the amino acids is based on SEQ ID NO:1 and wherein said mutein has reduced susceptibility for O-glycosylation when expressed in yeast compared to wild-type human FGF-21. Combining muteins with reduced susceptibility for O-glycosylation with any of embodiments of the present invention is within the scope of the present invention.

Moreover, U.S. patent application 60/528,582 discloses muteins comprising the substitution of a cysteine for two or more of the following: arginine 19, tyrosine 20, leucine 21, tyrosine 22, threonine 23, aspartate 24, aspartate 25, alanine 26, glutamine 27, glutamine 28, alanine 31, leucine 33, isoleucine 35, leucine 37, valine 41, glycine 42, glycine 43, glutamate 50, glutamine 54, leucine 58, valine 62, leucine 66, glycine 67, lysine 69, arginine 72, phenylalanine 73, glutamine 76, arginine 77, aspartate 79, glycine 80, alanine 81, leucine 82, glycine 84, serine 85, proline 90, alanine 92, serine 94, phenylalanine 95, leucine 100, aspartate 102, tyrosine 104, tyrosine 107, serine 109, glutamate 110, proline 115, histidine 117, leucine 118, proline 119, asparagine 121, lysine 122, serine 123, proline 124, histidine 125, arginine 126, aspartate 127, alanine 129, proline 130, glycine 132, alanine 134, arginine 135, leucine 137, proline 138, or leucine 139, wherein the numbering of amino acids is based on SEQ ID NO:1 and wherein said mutein has enhanced pharmaceutical stability compared to wild-type human FGF-21. Thus, combining muteins with enhanced pharmaceutical stability compared to wild-type human FGF-21 with any of the embodiments of the present invention is within the scope of the present invention.

Additionally, U.S. patent application 60/528,582 discloses muteins comprising the substitution of a charged and/or polar but uncharged amino acid for one or more of the amino acids at positions: glycine 42, glutamine 54, arginine 77, alanine 81, leucine 86, phenylalanine 88, lysine 122, histidine 125, arginine 126, proline 130, arginine 131, leucine 139, alanine 145, leucine 146, isoleucine 152, alanine 154, glutamine 156, glycine 161 serine 163, glycine 170, or serine 172, wherein the numbering of the amino acids is based on SEQ ID NO:1 and wherein said mutein has enhanced pharmaceutical stability compared to wild-type human FGF-21. Thus, combining muteins with enhanced pharmaceutical stability compared to wild-type human FGF-21 with any of the embodiments of the present invention is within the scope of the present invention.

A charged amino acid is defined as a positively or negatively charged amino acid. A positively charged amino acid is defined to include histadine, lysine, arginine, and non-naturally occurring analogs thereof (e.g., gamma aminobutyric acid, ornithine, etc.). A negatively charged amino acid is defined-to included aspartate, glutamate, and non-naturally occurring analogs thereof (e.g., aminoadipic acid). A polar but uncharged amino acid is defined to include serine, threonine, asparagine, glutamine, and non-naturally occurring analogs thereof.

Further embodiments of the present invention provide muteins of human FGF-21, or a biologically active peptide thereof, comprising a combination of the first, second, third, or fourth embodiment of the present invention with a mutein that has reduced susceptibility for O-glycosylation, a mutein that has enhanced pharmaceutical stability compared to wild-type human FGF-21 or any combination thereof.

Although the embodiments of the present invention concern muteins of FGF-21 having reduced susceptibility for proteolytic degradation when expressed in yeast compared to wild-type human FGF-21, maintaining the biological potency of the muteins as compared to wild-type FGF-21 is an important factor of consideration as well. Therefore, the biological potency of the muteins of the present invention is defined by the ability of the muteins to affect glucose uptake as measured in the in vitro 3T3-$L_1$ cell assay (Example 2) and/or the lowering of plasma glucose levels, as well as, plasma triglycerides, as measured in vivo in the ob/ob mouse assay (Example 3).

The muteins of FGF-21 administered according to this invention may be generated and/or isolated by any means known in the art. The most preferred method for producing the mutein is through recombinant DNA methodologies and is well known to those skilled in the art. Such methods are described in Current Protocols in Molecular Biology (John Wiley & Sons, Inc.), which is incorporated herein by reference.

Additionally, the preferred embodiments include a biologically active peptide derived from the mutein described herein. Such a peptide will contain at least one of the substitutions described and the mutein will possess biological activity. The peptide may be produced by any means known to those skilled in the art, examples of which included but are not limited to enzymatic digestion, chemical synthesis or recombinant DNA methodologies.

It is established in the art that fragments of peptides of certain fibroblast growth factors are biologically active. See for example, Baird et al., *Proc. Natl. Acad. Sci* (USA) 85:2324-2328 (1988), and *J. Cell. Phys. Suppl.* 5:101-106 (1987). Therefore, the selection of fragments or peptides of the mutein is based on criteria known in the art. For example, it is known that dipeptidyl peptidase IV (DPP-IV) is a serine type protease involved in inactivation of neuropeptides, endocrine peptides, and cytokines (Damme et al. *Chem. Immunol.* 72: 42-56, (1999)). The N-terminus of FGF-21 (His-ProIlePro) contains two dipeptides that could potentially be substrates to DPP-IV, resulting in a fragment of FGF-21 truncated at the N-terminus by up to 4 amino acids. This fragment of wild-type FGF-21 has been demonstrated to retain biological activity (U.S. patent application 60/528,582), thus, muteins of the present invention truncated at the N-terminus by up to 4 amino acids in combination with the amino acid substitutions of any of the embodiments of the present invention.

The present invention also encompasses polynucleotides encoding the above-described muteins that may be in the form of RNA or in the form of DNA, which DNA includes cDNA, genomic DNA, and synthetic DNA. The DNA may be double-stranded or single-stranded.

"Isolated polynucleotide" is understood as a polynucleotide that is isolated from the human body or otherwise produced by a technical process. The coding sequences that encode the muteins of the present invention may vary as a result of the redundancy or degeneracy of the genetic code.

The polynucleotides that encode for the muteins of the present invention may include the following: only the coding sequence for the mutein, the coding sequence for the mutein and additional coding sequence such as a functional polypeptide, or a leader or secretory sequence or a pro-protein sequence; the coding sequence for the mutein and non-coding sequence, such as introns or non-coding sequence 5' and/or 3' of the coding sequence for the mutein. Thus the term "polynucleotide encoding a mutein" encompasses a polynucleotide that may include not only coding sequence for the mutein but also a polynucleotide, which includes additional coding and/or non-coding sequence.

The present invention further relates to variants of the described polynucleotides that encode for fragments, analogs and derivatives of the polypeptide that contain the indicated substitutions. The variant of the polynucleotide may be a naturally occurring allelic variant of the human FGF-21 sequence, a non-naturally occurring variant, or a truncated variant as described above. Thus, the present invention also includes polynucleotides encoding the muteins described above, as well as variants of such polynucleotides, which variants encode for a fragment, derivative or analog of the disclosed mutein. Such nucleotide variants include deletion variants, substitution variants, truncated variants, and addition or insertion variants as long as at least one of the indicated amino acid substitutions of the embodiments of the instant invention are present.

The polynucleotides of the present invention will preferentially be expressed in fungal or yeast cells after the sequences have been operably linked to an expression control sequence. These expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

Yeast cells used for expressing the muteins of the present invention include *Pichia pastoris, Saccharomyces cerevisiae, Schizosaccharomyces pombe*, and *Pichia angust*. The yeast host cells contain suitable vectors with expression control sequences, such as promoters, including 3-phosphoglycerate kinase or other glycolytic enzymes, and an origin of replication, termination sequences and the like as desired. The preferred yeast host of the present invention is *Pichia pastoris* wherein the expression vector is integrated into the host chromosomal DNA. *Aspergillus niger, Trichoderma reesei*; and *Schizophyllum commune*, are examples of fungi hosts, although others may also be employed as a matter of choice.

The vectors containing the polynucleotide sequences of interest (e.g., the muteins of FGF-21 and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Various methods of protein purification may be employed and such methods are known in the art and described, for example, in Deutscher, *Methods in Enzymology* 182: 83-9 (1990) and Scopes, *Protein Purification: Principles and Practice*, Springer-Verlag, N.Y. (1982). The purification step(s) selected will depend, for example, on the nature of the production process used for the muteins of FGF-21.

The FGF-21 mutein-containing compositions should be formulated and dosed in a fashion consistent with good medical practice, taking into account the clinical condition of the patient, the site of delivery of the FGF-21 mutein composition, the method of administration, the scheduling of administration, and other factors known to practitioners. The "therapeutically effective amount" of the FGF-21 mutein for purposes herein is thus determined by such considerations The pharmaceutical compositions of the FGF-21 muteins of the present invention may be administered by any means known in the art that achieve the generally intended purpose: to treat type II diabetes, obesity, or metabolic syndrome. The preferred route of administration is parenteral, defined herein as referring to modes of administration that include intravenous, intramuscular, intraperitoneal, intrasternal, subcutaneous, and intraarticular injection and infusion. The dosage administered will be dependent upon the age, health, and weight of the recipient, kind of concurrent treatment, if any, frequency of treatment, and the nature of the effect desired. Compositions within the scope of the invention include all compositions wherein an FGF-21 mutein is present in an amount that is effective to achieve the desired medical effect for treatment type II diabetes, obesity, or metabolic syndrome. While individual needs may vary from one patient to another, the determination of the optimal ranges of effective amounts of all of the components is within the ability of the clinician of ordinary skill.

The muteins of FGF-21 of the present invention can be formulated according to known methods to prepare pharmaceutically useful compositions. A desired formulation would be one that is a stable lyophilized product that is reconstituted with an appropriate diluent or an aqueous solution of high purity with optional pharmaceutically acceptable carriers, preservatives, excipients or stabilizers [*Remington's Pharmaceutical Sciences* 16th edition (1980)]. The muteins of the present invention may be combined with a pharmaceutically acceptable buffer, and the pH adjusted to provide acceptable stability for administration.

For parenteral administration, the FGF-21 muteins are formulated generally by mixing one or more of them at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. Preferably, one or more pharmaceutically acceptable anti-microbial agents may be added. Phenol, m-cresol, and benzyl alcohol are preferred pharmaceutically acceptable anti-microbial agents.

Optionally, one or more pharmaceutically acceptable salts may be added to adjust the ionic strength or tonicity. One or more excipients may be added to further adjust the isotonicity of the formulation. Glycerin, sodium chloride, and mannitol are examples of an isotonicity adjusting excipient.

Those skilled in the art can readily optimize pharmaceutically effective dosages and administration regimens for therapeutic compositions comprising an FGF-21 mutein, as determined by good medical practice and the clinical condition of the individual patient. The appropriate dose of an FGF-21 mutein administered will result in lowering blood glucose levels and increasing energy expenditure by faster and more efficient glucose utilization, and thus is useful for treating type 2 diabetes, obesity and metabolic syndrome.

Furthermore, FGF-21 did not induce hypoglycemia in lean ZDF rats when compared to rats dosed with insulin (WO03/011213). This data indicates that FGF-21 affects plasma glucose levels in an insulin independent manner, and thus is also useful in the treatment of Type I diabetes.

In another aspect of the present invention, muteins of FGF-21 for use as a medicament for the treatment of type II diabetes, obesity, or metabolic syndrome, are contemplated.

Having now described the present invention in detail, the same will be more clearly understood by reference to the following examples, which are included herewith for purposes of illustration only and are not intended to be limiting of the invention.

All patents and publications referred to herein are expressly incorporated by reference.

EXAMPLE 1

Expression and Purification of FGF-21 Muteins in Yeast

FGF-21 muteins are expressed in yeast, such as *Pichia pastoris, Pichia methanolica* or *Saccharomyces cerevisiae*. For production in *Pichia pastoris* a commercially available system (Invitrogen, Carlsbad, Calif.) uses vectors with the powerful AOX1 (alcohol oxidase) promters to drive high-level expression of recombinant proteins. Alternatively, vectors that use the promoter from the GAP gene (glyceraldehyde-3-phosphate dehydrogenase) are available for high level constitutive expression. The multi-copy *Pichia* expression vectors allows one to obtain strains with multiple copies of the gene of interest integrated into the genome. Increasing the number of copies of the gene of interest in a recombinant *Pichia* strain can increase protein expression levels. Yet another yeast expression system is *Saccharomyces cerevisiae*. Expression vectors contain the promoter and enhancer sequences from the GAL1 gene. The GAL1 promoter is one of the most widely used yeast promoters because of its strong transcriptional activity upon induction with galactose.

Analytical characterization (mass spectrum analyses) indicates that the FGF-21 expressed in *Pichia pastoris* is truncated (four amino acid removal at the wild-type N-terminus). When assayed in the mouse 3T3-L1 adipocyte assay (see Example 2), this truncated variant of FGF-21 stimulates glucose uptake at the same level as wild-type FGF-21 (Table 1).

EXAMPLE 2

Glucose Uptake in Mouse 3T3-L1 Adipocytes

3T3-L1 cells are obtained from the American Type Culture Collection (ATCC, Rockville, Md.). Cells are cultured in growth medium (GM) containing 10% iron-enriched fetal bovine serum in Dulbecco's modified Eagle's medium. For standard adipocyte differentiation, two days after cells reached confluency (referred as day 0), cells are exposed to differentiation medium (DM) containing 10% fetal bovine serum, 10 µg/ml of insulin, 1 µM dexamethasone, and 0.5 µM isobutylmethylxanthine, for 48 h. Cells then are maintained in post differentiation medium containing 10% fetal bovine serum, and 10 µg/ml of insulin.

Glucose Transport Assay—Hexose uptake, as assayed by the accumulation of 0.1 mM 2-deoxy-D-[$^{14}$C]glucose, is measured as follows: 3T3-L1 adipocytes in 12-well plates are washed twice with KRP buffer (136 mM NaCl, 4.7 mM KCl, 10 mM NaPO$_4$, 0.9 mM CaCl$_2$, 0.9 mM MgSO$_4$, pH 7.4) warmed to 37° C. and containing 0.2% BSA, incubated in Leibovitz's L-15 medium containing 0.2% BSA for 2 h at 37° C. in room air, washed twice again with KRP containing, 0.2% BSA buffer, and incubated in KRP, 0.2% BSA buffer in the absence (Me$_2$SO only) or presence of wortmannin for 30 min at 37° C. in room air. Insulin is then added to a final concentration of 100 nM for 15 min, and the uptake of 2-deoxy-D-[$^{14}$C] glucose is measured for the last 4 min. Nonspecific uptake, measured in the presence of 10 µM cytochalasin B, is subtracted from all values. Protein concentrations are determined with the Pierce bicinchoninic acid assay. Uptake is measured routinely in triplicate or quadruplicate for each experiment.

In vitro potency is normalized to the in vitro activity of wild-type FGF-21, which is given a designation of 1.0 and used as a positive control. The in vitro potency of muteins of FGF-21 of the present invention is compared to wild-type FGF-21 in Table 1. As indicated in Table 1, the muteins of the present invention maintained biological potency to various degrees compare to wild-type FGF-21.

TABLE 1

| FGF-21 Mutein | Expression System | In vitro Potency |
| --- | --- | --- |
| Wild-type | E. coli | 1.0 |
| Truncated Wild-type* | Yeast | 0.9 |
| L153I* | HEK | 0.35 |
| L153E* | HEK | 0.64 |
| L153I* | Yeast | 0.05 |
| L153E* | Yeast | 0.13 |

*truncated by 4 amino acids at the N-terminus

EXAMPLE 3

Ob/ob Mouse Model

An obesity model using male ob/ob mice is used to monitor plasma glucose levels and triglyceride levels after treatment with FGF-21, compared to vehicle and insulin control groups. The test groups of male ob/ob mice (7 weeks old) are injected with vehicle alone (0.9% NaCl), or FGF-21 mutein (0.125 mg/kg) subcutaneously (0.1 mL, once daily) for seven days. Blood is collected by tail clip bleeding on day 7, one hour after the last compound injection and plasma glucose levels are measured using a standard protocol. The ability of the FGF-21 muteins of the present invention to lower plasma glucose levels as compared to the vehicle control is then determined.

EXAMPLE 4

Pharmaceutical Stability of FGF-21 Muteins

The stability of the FGF-21 muteins of the present invention is analyzed under simulated physiological and pharmaceutical formulation conditions. To simulate physiological conditions, the mutein is analyzed for stability in PBS at room temperature (RT) at a target protein concentration of 10 mg/ml, pH 7.4. Solubility/physical stability of the muteins in PBS is considered satisfactory if recovery of protein following preparation resulted in >90% recovery at RT as determined by size-exclusion and/or reversed-phase chromatography.

It is anticipated that pharmaceutical formulation of a mutein of the present invention will likely be a preserved multi-use formulation, thus, compatibility with a common preservative is analyzed. To test for formulation compatibility, a preservative, m-cresol, (3 mg/mL final concentration, a concentration usually sufficient to meet European Pharmacopia B criteria for preservative effectiveness under neutral pH conditions), is added at room temperature to a solution containing the mutein at approximately 10 mg/ml in PBS, pH 7.4. Physical stability in the presence of preservative is initially accessed by determining protien recovery of the main chromatographic peak after reversed-phase and size exclusion chromatography at RT. Furthermore, the extent of aggregation as measured by DLS (dynamic light scattering) at 37° C. is shown as the average diameter of particles in the presence of m-cresol after two hours, compared to wild-type FGF-21. A larger average diameter corresponds to an increased degree protein association and/or aggregation. Muteins of the present invention that are stable in PBS and compatible with preservative are designated to have enhanced or improved pharmaceutical properties as compared to wild-type FGF-21.

EXAMPLE 5

Analysis of Proteolytic Degradation

FGF-21 muteins are expressed in *Pichia pastoris* and are purified from the culture broth by HPLC (Waters 2695) using a Zorbax, 330-SB C8, 4.6×50 mm, 3.5 □m particle Column at 40° C. (Move Phase C: 0.1% TFA in 10% ACN and 90%H2O, D: 0.1% TFA in ACN). The following degradation products are identified: (1) 5-181; (2) 5-153; (3) 5-96

In addition, mass spectrometry analysis identifies other minor degradation fragments contaminating the final chromatography pools eluted from a Mono Q anion exchange column (Pharmacia). Such fragments are: (1) 5-174; (2) 5-175; (3) 5-177.

We claim:

1. The mutein of human FGF-21, or a biologically active peptide thereof, comprising the substitution of Leu 153 with Glu or Ile, in combination with the substitution of Ala for Ser 167, in combination with the substitution of a cysteine for leucine 118 and alanine 134 wherein the numbering of the amino acids is based on SEQ ID NO:1.

2. The mutein of claim 1 wherein said mutein is truncated at the N-terminus by up to 4 amino acids.

3. The mutein according to claim 2 wherein said mutein is desHisProIlePro/Leu118Cys/Ala134Cys/Ser167Ala/Leu153Ile.

4. A pharmaceutical composition comprising the following:
   (a) the FGF-21 mutein or a biologically active peptide thereof according to claim 3; and
   (b) an acceptable pharmaceutical carrier.

5. A method for treating a patient exhibiting obesity or type II diabetes comprising administering to said patient in need of such treatment a therapeutically effective amount of the FGF-21 mutein of claim 3.

6. A pharmaceutical composition comprising the following:
   (a) the FGF-21 mutein or a biologically active peptide thereof according to claim 2; and
   (b) an acceptable pharmaceutical carrier.

7. A method for treating a patient exhibiting obesity or type II diabetes comprising administering to said patient in need of such treatment a therapeutically effective amount of the FGF-21 mutein of claim 2.

8. A pharmaceutical composition comprising the following:
   (a) the FGF-21 mutein or a biologically active peptide thereof according to claim 1; and
   (b) an acceptable pharmaceutical carrier.

9. A method for treating a patient exhibiting obesity or type II diabetes comprising administering to said patient in need of such treatment a therapeutically effective amount of the FGF-21 mutein of claim 1.

* * * * *